United States Patent [19]

Anello et al.

[11] 4,374,782

[45] Feb. 22, 1983

[54] SYNTHESIS OF TRIFLUOROACETYL FLUORIDE

[75] Inventors: Louis G. Anello, Hamburg; Michael Van Der Puy, Cheektowaga; Martin A. Robinson, East Amherst; Richard E. Eibeck, Orchard Park, all of N.Y.

[73] Assignee: Allied Corporation, Morristown, N.J.

[21] Appl. No.: 275,009

[22] Filed: Jun. 18, 1981

[51] Int. Cl.³ .............................................. C07C 51/58
[52] U.S. Cl. .................................. 260/544 F; 568/386
[58] Field of Search ...................... 260/544 F, 544 Y; 568/20

[56] References Cited

U.S. PATENT DOCUMENTS

| | | | |
|---|---|---|---|
| 2,922,816 | 1/1960 | Bruce, Jr. ........................ | 260/544 F |
| 2,970,173 | 1/1961 | Howard et al. ....................... | 568/20 |
| 3,058,993 | 10/1962 | Carboni et al. ................. | 260/544 Y |
| 3,069,396 | 12/1962 | Middleton ............................. | 568/20 |
| 3,409,647 | 11/1968 | Pittman et al. .................. | 260/544 Y |
| 3,725,475 | 4/1973 | Paucksch et al. ............... | 260/544 Y |
| 4,334,099 | 6/1982 | De Puy et al. ....................... | 568/386 |

*Primary Examiner*—Natalie Trousof
*Assistant Examiner*—L. Hendriksen
*Attorney, Agent, or Firm*—Thomas D. Hoffman; Jay P. Friedenson

[57] ABSTRACT

A process for the preparation of trifluoroacetyl fluoride is disclosed, which comprises reacting, in the liquid phase, hexafluorothioacetone dimer in an aprotic solvent with at least a catalytic amount of an alkali metal fluoride in the presence of an oxidizing agent selected from the group consisting of $Ag_2O$, oxides of Pb, Sn, Ni, Co and Fe and $M_2S_2O_8$ wherein M is an alkali metal. The preferred aprotic solvent is dimethylformamide; the preferred alkali metal fluoride is KF; and the preferred oxidizing agents are $NiO$, $PbO_2$, and $M_2S_2O_8$ wherein M is Na or K.

10 Claims, No Drawings

SYNTHESIS OF TRIFLUOROACETYL FLUORIDE

DESCRIPTION

BACKGROUND OF THE INVENTION

The present invention relates to a process for preparation of trifluoroacetyl fluoride by reacting, in the liquid phase, hexafluorothioacetone dimer in an aprotic solvent such as dimethylformamide containing at least a catalytic amount of an alkali metal fluoride such as KF in the presence of an oxidizing agent selected from the group consisting of $Ag_2O$, oxides of Pb, Sn, Ni, Co and Fe and $M_2S_2O_8$ wherein M is an alkali metal such as Na or K.

Trifluoroacetyl fluoride is a known compound useful in the preparation of trifluoroacetic acid and the corresponding salts and esters which find utility as surface active agents and chemical intermediates.

U.S. Pat. No. 2,922,816 (Bruce) discloses a process for production of trifluoroacetyl fluoride by contacting, in the gaseous phase and at temperatures of 140° to 225° C., a mixture of tetrafluoroethylene and oxygen, preferably in a dilute mixture thereof, with a catalyst consisting of finely divided carbon and silver oxide supported on an inert carrier such as alumina or a metallic oxide or peroxide such as alkali earth oxides or peroxides which act as promoters. However, the expenses of the specially prepared silver oxide catalyst and the special apparatus required for this gas phase process which operates at elevated temperatures makes this process commercially unattractive.

Accordingly, it is an object of the present invention to provide a liquid phase process for the production of trifluoroacetyl fluoride which operates at milder reaction temperatures.

This and other objects and advantages of the present invention will be apparent from the description which follows.

SUMMARY OF THE INVENTION

In accordance the present invention, there is provided a process for the preparation of the trifluoroacetyl fluoride, which comprises reacting, in the liquid phase, hexafluorothioacetone dimer in an aprotic solvent containing at least a catalytic amount of an alkali metal fluoride in the presence of an oxidizing agent selected from the group consisting of $Ag_2O$, oxides of Pb, Sn, Ni, Co and Fe and $M_2S_2O_8$ wherein M is an alkali metal.

DETAILED DESCRIPTION OF THE PRESENT INVENTION AND OF THE PREFERRED EMBODIMENTS

The present invention provides a one step liquid phase process for the preparation of trifluoroacetyl fluoride by dissolving hexafluorothioacetone dimer, a stable liquid ($bp_{760}$ 110° C.), in an aprotic solvent such as dimethylformamide containing at least a catalytic amount of an alkali metal fluoride such as KF and at least about a stoichiometric amount of a selected metallic oxide or alkali metal persulfate oxidizing agent. The heterogeneous reaction mixture so formed is heated, with agitation, at elevated temperatures for a time sufficient to convert the hexafluorothioacetone dimer into trifluoroacetyl fluoride which is conveniently collected in a cold trap connected to the reaction apparatus.

The oxidizing agents found useful in the present invention are selected from the group consisting of $Ag_2O$, oxides of Pb, Sn, Ni, Co and Fe and persulfates having formula $M_2S_2O_8$ wherein M is an alkali metal. Exemplary of the metallic oxide oxiding agents are $Ag_2O$, PbO, $PbO_2$, SnO, $SnO_2$, NiO, CoO, $Co_3O_4$, FeO, and $Fe_2O_3$; $PbO_2$ and NiO are preferred. Exemplary of the alkali metal persulfates are $Na_2S_2O_8$, $Li_2S_2O_8$ and $K_2S_2O_8$ and $Cs_2S_2O_8$. For economic reasons $Na_2S_2O_8$ and $K_2S_2O_8$ are preferred; $K_2S_2O_8$ is more preferred.

Among the aprotic solvents found useful in the present invention are dimethylformamide, dimethylacetamide, dimethyl sulfoxide, acetonitrile and N-methyl pyrrolidone. Dimethylformamide is the preferred aprotic solvent.

Since trifluoroacetyl fluoride very readily hydrolyzes to form trifluoroacetic acid, the aprotic solvent and other reagents, such as starting material, hexafluorothioacetone dimer, as well as the reactor, should preferably be dry in order to obtain a good yield of trifluoroacetyl fluoride essentially free of the corresponding acid. Specifically, the total reactor including all reactants and the aprotic solvent should preferably be dry, i.e., total water content should be no more than about 0.05% by weight of water.

The alkali metal fluoride found useful in the generation of trifluoroacetyl fluoride from hexafluorothioacetone dimer in an aprotic solvent such as dimethylformamide includes LiF, NaF, CsF and KF. Since KF is more soluble in dimethylformamide, KF is the preferred alkali metal fluoride. The effective amount of alkali metal fluoride varies with the water content of the reaction mixture. When the water content in the reaction mixture, and specifically the aprotic solvent, preferably dimethylformamide, is maintained at the preferred value of no more than about 0.05 weight % of water, the catalytic amount of alkali metal fluoride is between about 0.06–5 moles, preferably 0.06–1 moles of alkali metal fluoride per one mole of hexafluorothioacetone dimer. An upper limit on the catalytic amount of alkali metal fluoride, preferably KF, is not critical; an amount of alkali metal fluoride, preferably KF, in excess of 0.06 mole per one mole of hexafluorothioacetone dimer is effective. When the water content of the reaction mixture, specifically of the aprotic solvent, is maintained at no more than about 0.05 weight %, only economic considerations would preclude employing a catalytic amount of alkali metal fluoride, preferably KF, in excess of 5 moles per one mole of the hexafluorothioacetone dimer.

The molar ratio of oxidizing agent to hexafluorothioacetone dimer is not critical. However, at least a stoichiometric amount of oxidizing agent is preferably present per stoichiometric amount of hexafluorothioacetone dimer. Generally for the oxidizing agents such as PbO, NiO, SnO, FeO, CoO, the preferred stoichiometric amount is about 2 moles of oxidizing agent per mole of hexafluorothioacetone dimer; for the oxidizing agents such as $PbO_2$, $SnO_2$, and $M_2S_2O_8$ wherein M is alkali metal, the preferred stoichiometric amount is about 1 mole of oxidizing agent per mole of hexafluorothioacetone dimer.

Reaction temperatures are not critical. Temperatures in the range of about 75° to about 150° C. are adequate for the present invention; temperatures of about 100° C. to about 130° C. are preferred.

Reaction times are not critical. Conveniently, reaction times of about 3 to about 5 hours are employed.

The concentrations of hexafluorothioacetone dimer and oxidizing agent in aprotic solvent are not critical. Sufficient aprotic solvent should be present to permit agitation and maintain fluidity in the reaction mixture.

The desired trifluoroacetyl fluoride is conveniently allowed to distill out of the reaction mixture and is collected in a cold trap. Purification of trifluoroacetyl fluoride (bp −59° C.) to remove sideproducts such as hexafluoroacetone is conveniently accomplished conventionally by fractional distillation or gas chromatography. Sufficiently high pressure and sufficiently low temperatures should be employed to condense the trifluoroacetyl fluoride.

EXAMPLE 1

Into a 100 mL, 3 neck flask fitted with thermometer, stirrer and a reflux condenser connected to a dry ice-acetone trap was charged 25 g (0.073 mole) of

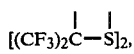

20 g (0.083 mole) of PbO$_2$, 6 g (0.10 mole) of anhydrous KF and 30 mL of dimethylformamide which had been dried (freshly distilled from P$_2$O$_5$) in accordance with procedure of T. Kitazume et al., Chemistry Letters, 267 (1973). The mixture was heated to 110° C. to 135° C. for 5 hours, and 16 g (0.138 mole) of CF$_3$COF was collected for a 99% conversion and yield. Trace amounts of hexafluoroacetone were also detected in the infrarad (IR) spectrum of the recovered product.

EXAMPLE 2

Following the procedure of Example 1, 25 g (0.07 mole) of

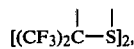

20 g (0.073 mole) K$_2$S$_2$O$_8$, 6 g (0.10 mole) KF and 30 mL of dried dimethylformamide were heated to 110°–130° C. for 5 hours. There was recovered 20 g of low boiler in the −78° C. trap. Infrared spectrum analysis and GLC analysis indicated the presence of 14 g (0.12 mole) CF$_3$COF for an 86% conversion and 2 g (0.012 mole) of CF$_3$COCF$_3$ for an 8% conversion.

EXAMPLE 3

Following the procedure of Example 1, 133 g (0.366 mole) of

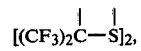

155 g (0.69 mole) of PbO, 16 g (0.285 mole) of KF and 130 mL of dried dimethylformamide were heated with stirring to 110°–130° C. for 5 hours. There was recovered 60 g of condensate in the −78° C. trap. The condensate was distilled to give 22 g (0.19 mole) of CF$_3$COF for a 26.14% conversion and 29 g (0.17 mole) of CF$_3$COCF$_3$ for a 24.76% conversion.

EXAMPLE 4

Following the procedure of Example 1, 20 g (0.055 mole) of

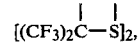

25 g (0.33 mole) NiO, 6 g (0.10 mole) anhydrous KF and 30 mL dried dimethylformamide were heated to 110°–140° C. over a 5 hour period. There was recovered 11 g (0.095 mole) of CF$_3$COF in the dry ice-acetone trap for an 86% conversion.

EXAMPLE 5

Following the procedure, of Example 1, 25 g (0.07 mole)

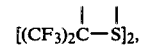

20 g (0.11 mole) SnO, 6 g (0.10 mole) anhydrous KF and 30 mL dried dimethylformamide were heated to 110°–140° C. over a 3 hour period. There was recovered 14 g of condensate in the dry ice-acetone trap. The IR and GLC of the sample showed a 50/50 mixture of CF$_3$COF and CF$_3$COCF$_3$.

EXAMPLE 6

Following the procedure of Example 1, 106 g (0.29 mole) of

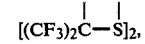

44 g (0.27 mole) of Fe$_2$O$_3$, 10.6 g (0.18 mole) of anhydrous KF and 150 mL of dried dimethylformamide were heated to 110°–145° C. over a 5 hour period. There were recovered 52 g condensate in the dry ice-acetone trap which was shown to be, by IR and GLC, a 50/50 mixture of CF$_3$COF and CF$_3$COCF$_3$.

EXAMPLE 7

A 500 mL, 3-necked flask was fitted with a mechanical stirrer, thermometer, and a water-cooled condenser. The outlet of the condenser was attached to a −78° C. cold trap. Under an atmosphere of nitrogen, the flask was charged with 6.0 g anhydrous KF, 34.2 g (0.148 mole) Ag$_2$O, 14.0 g (86 wt.% purity, 0.033 mole) hexafluorothioacetone dimer,

and 80 mL dried dimethylformamide. The reaction was stirred at a temperature of 110° to 140° C. for 6 hours. In the cold trap, 12.0 g crude product was collected and analyzed by GC and IR to contain 80 wt % hexafluoroacetone and 20 wt % CF$_3$COF. The yield of CF$_3$COCF$_3$ was 88%.

EXAMPLE 8

The procedure of Example 7 was employed excepting that AgO was used in place of Ag$_2$O. The flask was charged with 70 g (0.19 moles) of

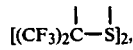

50 g (0.40 moles) of AgO, 6 g anhydrous KF and 130 mL of dried dimethylformamide. The crude product (36 g) was collected and analyzed by GC and IR to contain 73 wt % CF$_3$COCF$_3$ and 4% (CF$_3$)$_3$CH. No CF$_3$COF was detected.

EXAMPLES 9–50

In the following examples, the procedure and apparatus of Example 1 are employed excepting that the oxidizing agent, aprotic solvent and alkali metal fluoride are varied as indicated in the following Table.

TABLE 1

| Example | Oxidizing Agent | Aprotic Solvent | Alkali Metal Fluoride |
|---|---|---|---|
| 9 | PbO$_2$ | DMF[1] | LiF |
| 10 | " | " | NaF |
| 11 | " | " | CsF |
| 12 | " | DMSO[2] | KF |
| 13 | " | DMAC[3] | " |
| 14 | " | NMP[4] | " |
| 15 | K$_2$S$_2$O$_8$ | DMSO | " |
| 16 | " | DMAC | " |
| 17 | " | NMP | " |
| 18 | Na$_2$S$_2$O$_8$ | DMF | NaF |
| 19 | " | DMSO | " |
| 20 | " | DMAC | " |
| 21 | " | NMP | " |
| 22 | NiO | DMSO | KF |
| 23 | " | DMAC | " |
| 24 | " | NMP | " |
| 25 | PbO | DMF | " |
| 26 | " | DMSO | " |
| 27 | " | DMAC | " |
| 28 | " | NMP | " |
| 29 | SnO | DMSO | NaF |
| 30 | " | DMAC | " |
| 31 | " | NMP | " |
| 32 | SnO$_2$ | DMF | LiF |
| 33 | " | DMSO | " |
| 34 | " | DMAC | " |
| 35 | " | NMP | " |
| 36 | CoO | DMF | KF |
| 37 | " | DMSO | " |
| 38 | " | DMAC | " |
| 39 | " | NMP | " |
| 40 | Co$_3$O$_4$ | DMF | NaF |
| 41 | " | DMSO | " |
| 42 | " | DMAC | " |
| 43 | " | NMP | " |

TABLE 1-continued

| Example | Oxidizing Agent | Aprotic Solvent | Alkali Metal Fluoride |
|---|---|---|---|
| 44 | Fe$_2$O$_3$ | DMSO | KF |
| 45 | " | DMAC | " |
| 46 | " | NMP | " |
| 47 | FeO | DMF | NaF |
| 48 | " | DMSO | " |
| 49 | " | DMAC | " |
| 50 | " | NMP | " |

FOOTNOTES TO TABLE 1
[1]DMF is dimethylformamide
[2]DMSO is dimethyl sulfoxide
[3]DMAC is dimethylacetamide
[4]NMP is N—methyl pyrrolidone

We claim:

1. A process for the preparation of trifluoroacetyl fluoride, which comprises reacting, in the liquid phase under substantially dry conditions and at elevated temperatures, hexafluorothioacetone dimer in an aprotic solvent containing at least a catalytic amount of an alkali metal fluoride with an oxidizing agent selected from the group consisting of oxides of Pb, Sn, Ni, Co and Fe and M$_2$S$_2$O$_8$ wherein M is an alkali metal.

2. The process of claim 1 wherein the oxidizing agent is selected from the group consisting of PbO, PbO$_2$, SnO, SnO$_2$, FeO, Fe$_2$O$_3$, NiO, CoO, Co$_3$O$_4$, K$_2$S$_2$O$_8$ and Na$_2$S$_2$O$_8$.

3. The process of claim 2 wherein the aprotic solvent is selected from the group consisting of acetonitrile, dimethylacetamide, dimethylformamide, dimethyl sulfoxide and N-methyl pyrrolidone.

4. The process of claim 2 wherein the oxidizing agent is PbO$_2$ and wherein the aprotic solvent is dimethylformamide.

5. The process of claim 2 wherein the oxidizing agent is NiO and wherein the aprotic solvent is dimethylformamide.

6. The process of claim 2 wherein the oxidizing agent is Na$_2$S$_2$O$_8$ and wherein the aprotic solvent is dimethylformamide.

7. The process of claim 2 wherein the oxidizing agent is K$_2$S$_2$O$_8$ and wherein the aprotic solvent is dimethylformamide.

8. The process of claim 4 or 5 or 6 or 7 wherein the alkali metal fluoride is KF and wherein the molar ratio of hexafluorothioacetone dimer to KF is at least about 0.06:1 to about 1:1.

9. The process of claim 4 or 5 or 6 or 7 wherein the molar ratio of said oxides to hexafluorothioacetone dimer is about 2:1.

10. The process of claim 2 which further comprises agitating the reaction mixture.

* * * * *